United States Patent
Damavarapu et al.

(10) Patent No.: US 9,643,937 B1
(45) Date of Patent: May 9, 2017

(54) ONE-POT PROCESS FOR PREPARATION OF AMMONIUM AND HYDROXYL AMMONIUM DERIVATIVES OF BIS 5,5'-TETRAZOLE-1,1'-DIHYDROXIDE

(71) Applicant: The United States of America as Represented by the Secretary of the Army, Washington, DC (US)

(72) Inventors: Reddy S. Damavarapu, Hackettstown, NJ (US); Raja G. Duddu, Hackettstown, NJ (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 15/086,994

(22) Filed: Mar. 31, 2016

(51) Int. Cl.
*C07D 257/04* (2006.01)

(52) U.S. Cl.
CPC ................. *C07D 257/04* (2013.01)

(58) Field of Classification Search
None
See application file for complete search history.

(56) References Cited

U.S. PATENT DOCUMENTS

| 5,476,967 A | 12/1995 | Kanno et al. |
| 2014/0171657 A1 | 6/2014 | Klapotke et al. |

OTHER PUBLICATIONS

Fischer, Niko et al, Nitrogen-Rich Salts of 1H, 1'H-5,5'-Bitetrazole-1,1'-diol; Energetic Materials with High Thermal Stability, European Journal of Inorganic Chemistry, 2013, 2167-2180, Wiley-VCH Verlag GmbH & Co. KGaA, Weinheim.
Fischer, Niko et al, Pushing the Limits of Energetic Materials—the Synthesis and Characterization of Dihydroxylammonium 5,5'-bistetrazole-1,1∝diolate, Journal of Materials Chemistry, 2012, 20418-20422, vol. 22, The Royal Society of Chemistry.
Brinck, Tore, Green Energetic Materials, School of Chemical Science and Engineering, KTH Royal Institute of Technology, Sweden, 2014, 133-177, John Wiley & Sons, Ltd.

*Primary Examiner* — Alicia L Otton
(74) *Attorney, Agent, or Firm* — Lisa H. Wang

(57) ABSTRACT

A one-pot process for preparing ammonium and hydroxylammonium salts of bis 5,5'-tetrazole-1,1'-dihydroxide, specifically, diammonium bis 5,5'-tetrazole-1,1'-diolate (ABTOX) and dihydroxylammonium 5,5'-bistetrazole-1,1'-diolate (TKX-50). The process requires the reaction of sodium azide, dichloroglyoxime, HCl in dioxane solution to form bis 5,5'-tetrazole-1,1'-dihydroxide and treating this product with either ammonium chloride to produce ABTOX or hydroxylamine hydrochloride to produce TKX-50.

3 Claims, No Drawings

ONE-POT PROCESS FOR PREPARATION OF AMMONIUM AND HYDROXYL AMMONIUM DERIVATIVES OF BIS 5,5'-TETRAZOLE-1,1'-DIHYDROXIDE

RIGHTS OF THE GOVERNMENT

The inventions described herein may be manufactured and used by or for the United States Government for government purposes without payment of any royalties.

FIELD OF INVENTION

A one-pot process for producing diammonium bis 5,5'-tetrazole-1,1'-diolate (ABTOX) and dihydroxyammonium 5,5'-bistetrazole-1,1'-diolate (TKX-50) by preparing and reacting its precursor bis 5,5'-tetrazole-1,1'-dihydroxide with ammonium chloride or hydroxylamine hydrochloride respectively.

BACKGROUND OF THE INVENTION

Energetics compounds have many civil and military applications. Popular energetic materials include 1,3,5-hexahydro-1,3,5-trinitro triazine (RDX) which was use as explosives during World War II and in industrial applications for demolitions. RDX, however, is a nitroamine based compound which is known to degrade into toxic by-products. Alternative energetics such as derivatives of tetrazole offer certain advantages over RDX. For instance, tetrazole compounds have desirable energetic characteristics due in part to its C—N and N—N bonds. Such chemistry lends itself to exhibiting high density, high thermal stability, and low sensitivities towards impact, friction, and electrical discharge. Tetrazole compounds release relatively benign by-products upon decomposition and also provide environmentally beneficial nitrogen gases as a decomposition product. An example of a tetrazole based compound is bis 5,5'-tetrazole-1,1'-dihydroxide. Ammonium and hydroxylammonium salts of bis 5,5'-tetrazole-1,1'-dihydroxide, including diammonium his 5,5'-tetrazole-1,1'-diolate (ABTOX) and dihydroxyammonium 5,5'-bistetrazole-1,1'-diolate (TKX-50) respectively are known to be suitable replacements for RDX as an energetic material.

While bis 5,5'-tetrazole-1,1'-dihydroxide based salts are desirable energetic compounds, the reported methods for producing such compounds are dangerous because it requires toxic reactant materials and it yields highly energetic intermediates. For instance, the first reaction step requires bubbling chlorine, a toxic gas, into an ethanolic solution of glyoxime at low temperatures (<−30° C.) to obtain dichloroglyoxime. Reaction of this dichloroglyoxime with sodium azide in dimethylformamide provides diazidoglyoxime. Hydrogen chloride (HCl) gas is then bubbled into an ethereal solution of diazidoglyoxime until saturation of the medium to produce dimethylammonium salts of bis-dihydroxytetrazoles. Diazidoglyoxime, an intermediate, produced during this process is highly sensitive and has characteristics of a primary explosive.

The reaction process reported above may be functional in small laboratory scale setting, however, it poses significant risks for large scale preparations due to the vague criteria of bubbling the HCl gas in the reaction medium "until saturation." This leads to uncertainty as to the amount of time and reagents necessary to reach "saturation." Uncertain reaction conditions particularly with respect to energetic materials may lead to detonation creating hazardous and unsafe working condition.

Thus, a need exist for an improved processes for producing ammonium and hydroxyl ammonium derivatives of bis 5,5'-tetrazole-1,1'-dihydroxide that minimizes utilization and handling of toxic and hazardous compounds.

SUMMARY OF THE INVENTION

Disclosed herein is a one-pot process for synthesis of ABTOX and TKX-50. The process utilizes a reaction comprising sodium azide, dichloroglyoxime, DMF and HCl in dioxane solution to form dimethylammonium salts of bis-dihydroxytetrazoles. The resulting product is further reacted with either ammonium chloride to produce ABTOX or hydroxylamine hydrochloride to produce TKX-50.

DETAILED DESCRIPTION

Disclosed herein is a one pot process for preparing ammonium and hydroxylammonium salts of bis 5,5'-tetrazole-1,1'-dihydroxide. The improved process eliminates usage of toxic and hazardous chemicals such as chlorine and hydrogen chloride in gaseous forms, and highly flammable diethyl ether solvent from the reaction process as previously reported.

Scheme 1 below illustrates the process for preparing ammonium and hydroxylammonium salts of bis 5,5'-tetrazole-1,1'-dihydroxide. Specifically, a cold solution of glyoxime (1) in DMF was treated with N-chlorosuccinimide (NCS) and the reaction mixture was allowed to stir at room temperature for 12 h. After this period, the reaction mixture was cooled to about 3° C. Sodium azide preferably in solid form was slowing added to the cold solution so that the temperature of the reaction mixture remained below 15° C. After addition had been completed, the reaction mixture was stirred at this temperature for 3-48 hours, preferably for 4 hours, at which point the mixture was again cooled in an ice bath. A commercially available solution of 4M HCl in dioxane was added dropwise to the reaction mixture. After stirring the reaction mixture at room temperature for 16 h, it was diluted with water and evaporated to dryness. The residue was treated with water and heated to boiling until a clear homogeneous solution was obtained which was immediately treated with an aqueous solution of ammonium chloride in the case of 2 or hydroxyammonium chloride in the case of 3. The solid crystalline product 2 or 3 was isolated via filtration. The spectral data of 2 and 3 matches with values reported in the literature.

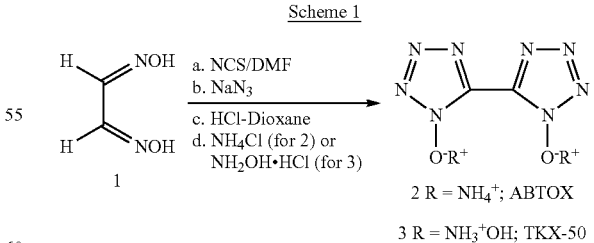

Scheme 1 a. NCS/DMF
b. NaN$_3$
c. HCl-Dioxane
d. NH$_4$Cl (for 2) or NH$_2$OH·HCl (for 3)

2 R = NH$_4^+$; ABTOX

3 R = NH$_3^+$OH; TKX-50

Preparation of diammonium bis 5,5'-tetrazole-1,1'-diolate (ABTOX)

A solution of dichloroglyoxime is prepared by adding a cold (3° C.) solution of glyoxime (1.40 g, 16 mmol) in N, N-dimethylformamide (20 ml) to N-chlorosuccinimide (4.46 g, 33.6 mmol). The reaction mixture was allowed to attain room temperature and then stirred for 12 hours. It was then again cooled to in an ice bath to 3° C. To this cold reaction mixture solid sodium azide (2.24 g, 34.4 mmol) was added in small portion <15° C. The reaction mixture was allowed to stir at 15° C. for 4 hours and then was cooled again in an ice bath. To the reaction mixture was then added dropwise a solution of 4M HCl in dioxane (90 mL) while maintaining the reaction temperature below 15° C. After the addition had been completed, the reaction mixture was sealed with stoppers and stirred at room temperature for 16 h. The reaction mixture was treated with water (10 ml) and evaporated on a rotary evaporator under high vacuum to dryness. The residue was treated with water (25 ml) and again evaporated to dryness. The resulting semi-solid residue was treated with water (20 ml) and boiled to get a clear homogeneous solution (HS).

To the above hot solution (HS) was added a solution of ammonium chloride (2.54 g, 48 mmol) in water (10 ml). The resulting solution was kept aside for 2.5 h at room temperature. The solid formed was separated via filtration. The solid was washed with cold water (2×5 ml), ethanol (1×5 ml) and air dried at room temperature. The pure product was obtained in 70% (2.30 g) as off white crystalline solid. $^{13}$C NMR (DMSO-$d_6$): 134.30

Preparation of dihydroxylammonium
5,5'-bistetrazole-1,1'-diolate (TKX-50)

The reaction was carried out in an identical manner as mentioned above for ABTOX preparation until the point of obtaining a clear homogeneous solution (HS). The hot solution (HS) was then treated with a solution of hydroxylamine hydrochloride (2.42 g, 35.2 mmol) in water (11 ml) and heated again to boil. Then the solution was kept aside at room temperature for 2 h. The white crystalline solid was separated via filtration and washed with water (2×10 ml), ethanol (1×10 ml) and air dried at room temperature. The pure product was obtained in 71% (2.69 g) as a white crystalline solid. $^{13}$C NMR (DMSO-$d_6$): 134.93

While embodiments have been set forth as illustrated and described above, it is recognized that numerous variations may be made with respect to amounts of the various constituents in the composition. Therefore, while the invention has been disclosed in various forms only, it will be obvious to those skilled in the art that additions, deletions and modifications can be made without departing from the spirit and scope of this invention, and no undue limits should be imposed, except as to those set forth in the following claims.

What is claimed is:

1. A one-pot process for preparing bis 5,5'-tetrazole 1,1'-dihydroxide comprising the following steps:
    (a) adding sodium azide to a solution comprising dichloroglyoxime;
    (b) stirring the solution at less than 15° C.;
    (c) adding hydrochloric acid dissolved in dioxane to the solution of step (b) and maintaining the temperature of the solution at less than 15° C.;
    (d) mixing the solution with water;
    (e) removing the liquid from the solution to isolate solid bis 5,5'-tetrazole-1,1'-dihydroxide.

2. A one-pot process for preparing diammonium bis 5,5'-tetrazole-1,1'-diolate (ABTOX) comprising the following steps:
    (a) adding water to the product produced by the process of claim 1 to form a mixture;
    (b) heating the mixture to a clear homogenous solution;
    (c) reacting an aqueous solution of ammonium chloride to the clear homogenous solution to form ABTOX; and
    (d) separating the solid ABTOX from the solution.

3. A one-pot process for preparing dihydroxylammonium 5,5'-bistetrazole-1,1'-diolate (TKX-50) comprising the following steps:
    (a) adding water to the product produced by the process of claim 1 to form a mixture;
    (b) heating the mixture to a clear homogenous solution;
    (c) adding an aqueous solution of hydroxylamine hydrochloride to the reaction pot;
    (d) heating the mixture of step (c) to the boiling point;
    (e) cooling the mixture and separating the solid TKX-50 from the solution.

* * * * *